(12) United States Patent
Medoff et al.

(10) Patent No.: US 10,011,625 B2
(45) Date of Patent: Jul. 3, 2018

(54) PROCESSING FACILITY

(71) Applicant: XYLECO, INC., Wakefield, MA (US)

(72) Inventors: Marshall Medoff, Brookline, MA (US); Thomas Craig Masterman, Rockport, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

(21) Appl. No.: 15/141,605

(22) Filed: Apr. 28, 2016

(65) Prior Publication Data

US 2016/0237393 A1 Aug. 18, 2016

Related U.S. Application Data

(63) Continuation of application No. 15/141,281, filed on Apr. 28, 2016, now Pat. No. 9,493,495, which is a
(Continued)

(51) Int. Cl.
*C12M 1/00* (2006.01)
*C07G 1/00* (2011.01)
(Continued)

(52) U.S. Cl.
CPC ............ *C07G 1/00* (2013.01); *C08B 37/0003* (2013.01); *C08H 8/00* (2013.01); *C10L 1/02* (2013.01);
(Continued)

(58) Field of Classification Search
CPC ........ C07G 1/00; C08B 37/0003; C08H 8/00; C10L 1/02; C10L 1/026; C12M 21/12;
C12M 29/00; C12M 33/00; C12M 35/02; C12M 41/00; C12M 41/32; C12M 41/36; C12M 45/02; C12M 45/06; C12M 45/07; C12M 45/09; C12P 7/02; C12P 7/10;
(Continued)

(56) References Cited

U.S. PATENT DOCUMENTS 3,801,432 A * 4/1974 Free .................. D21C 1/00
162/50
4,000,032 A 12/1976 Bergstrom et al.
(Continued)

FOREIGN PATENT DOCUMENTS

JP 5856691 4/1983
JP 06-316888 11/1994
(Continued)

OTHER PUBLICATIONS

Search Report—Corresponding Eurasian Application No. 201600055, dated Apr. 28, 2016, 6 pages.
(Continued)

*Primary Examiner* — Xiuyu Tai
(74) *Attorney, Agent, or Firm* — Leber IP Law; Shelly M. Fujikawa

(57) ABSTRACT

Biomass feedstocks (e.g., plant biomass, animal biomass, and municipal waste biomass) are processed to produce useful products, such as fuels. For example, systems are described that can use feedstock materials, such as cellulosic and/or lignocellulosic materials and/or starchy materials, to produce a product or intermediate, e.g., energy, a food, a fuel, or a material.

8 Claims, 4 Drawing Sheets

Related U.S. Application Data continuation of application No. 14/887,153, filed on Oct. 19, 2015, now Pat. No. 9,353,344, which is a continuation of application No. 14/494,815, filed on Sep. 24, 2014, now Pat. No. 9,181,567, which is a continuation of application No. 13/786,920, filed on Mar. 6, 2013, now Pat. No. 8,877,467, which is a continuation of application No. 12/704,519, filed on Feb. 11, 2010, now Pat. No. 8,415,122.

(60) Provisional application No. 61/151,724, filed on Feb. 11, 2009.

(51) Int. Cl.

| | |
|---|---|
| C08H 8/00 | (2010.01) |
| C10L 1/02 | (2006.01) |
| C12P 7/10 | (2006.01) |
| C12P 7/40 | (2006.01) |
| C12P 7/62 | (2006.01) |
| C12P 19/14 | (2006.01) |
| C12P 7/02 | (2006.01) |
| C12M 1/26 | (2006.01) |
| C12M 1/42 | (2006.01) |
| C12M 1/34 | (2006.01) |
| C08B 37/00 | (2006.01) |
| C12P 7/54 | (2006.01) |
| C13K 1/02 | (2006.01) |
| C12M 1/33 | (2006.01) |
| C12P 19/04 | (2006.01) |

(52) U.S. Cl.
CPC ............ *C10L 1/026* (2013.01); *C12M 21/12* (2013.01); *C12M 29/00* (2013.01); *C12M 33/00* (2013.01); *C12M 35/02* (2013.01); *C12M 41/00* (2013.01); *C12M 41/32* (2013.01); *C12M 41/36* (2013.01); *C12M 45/02* (2013.01); *C12M 45/06* (2013.01); *C12M 45/07* (2013.01); *C12M 45/09* (2013.01); *C12P 7/02* (2013.01); *C12P 7/10* (2013.01); *C12P 7/40* (2013.01); *C12P 7/54* (2013.01); *C12P 7/62* (2013.01); *C12P 19/04* (2013.01); *C12P 19/14* (2013.01); *C13K 1/02* (2013.01); *C10G 2300/1014* (2013.01); *C12P 2201/00* (2013.01); *C12P 2203/00* (2013.01); *Y02E 50/13* (2013.01); *Y02E 50/16* (2013.01); *Y02E 50/17* (2013.01); *Y02E 50/30* (2013.01); *Y02P 30/20* (2015.11); *Y02T 50/678* (2013.01)

(58) Field of Classification Search
CPC ........... C12P 7/40; C12P 7/54; C12P 2201/00; C12P 2203/00; C12P 19/02; C12P 7/62; C12P 19/04; C12P 19/14; C13K 1/02; Y02P 30/20; C10G 2300/1014; Y02E 50/13; Y02E 50/16; Y02E 50/17; Y02T 50/678; C12N 13/00; C12N 9/2437; C12Y 302/01004

See application file for complete search history.

(56) References Cited

U.S. PATENT DOCUMENTS

| | | |
|---|---|---|
| 4,304,649 A | 12/1981 | Han et al. |
| 5,196,069 A | 3/1993 | Cullingford et al. |
| 6,555,350 B2 | 4/2003 | Ahring et al. |
| 8,168,038 B2 | 5/2012 | Medoff |
| 8,415,122 B2 | 4/2013 | Medoff et al. |
| 8,597,921 B2 | 12/2013 | Medoff |
| 8,603,787 B2 | 12/2013 | Medoff |
| 8,609,384 B2 | 12/2013 | Medoff |
| 8,852,901 B2 | 10/2014 | Medoff et al. |
| 9,181,567 B2 | 11/2015 | Medoff |
| 2006/0088922 A1 | 4/2006 | Yang et al. |
| 2006/0196622 A1 | 9/2006 | Trung et al. |
| 2011/0027837 A1 | 2/2011 | Medoff |
| 2011/0039317 A1 | 2/2011 | Medoff |
| 2012/0052536 A1 | 3/2012 | Medoff et al. |
| 2012/0237984 A1 | 9/2012 | Medoff |
| 2012/0309060 A1 | 12/2012 | Medoff |

FOREIGN PATENT DOCUMENTS

| | | | |
|---|---|---|---|
| JP | 2005289666 | | 10/2005 |
| JP | 2008092910 | | 4/2008 |
| RU | 2095415 | | 11/1997 |
| WO | 2004063382 | | 7/2004 |
| WO | WO2006/017137 | * | 2/2006 |
| WO | 2007054610 | | 5/2007 |
| WO | 2008073186 | | 6/2008 |

OTHER PUBLICATIONS

Sun, R.C. et al., "Comparative Study of Lignins Isolated by Alkali and Ultrasound-Assisted Alkali Extractions from Wheat Straw", Ultrasonics Sonochemistry, Mar. 2002, vol. 9, No. 2, pp. 85-93.

Search Report—Corresponding Singapore Application No. 2014007140, dated Jan. 15, 2016, 9 pages.

Gould, J. Michael et al., "High Efficiency Ethanol Production from Lignocellulosic Residues Pretreated with Alkaline H2O2", Biotechnology and Bioengineering, vol. XXVI, 1984, pp. 628-631.

Saha, Badal C. et al., "Dilute Acid Pretreatment, Enzymatic Saccharification and Fermentation of Wheat Straw to Ethanol", Process Biochemistry, vol. 40, 2005, pp. 3693-3700.

Taherzadeh et al., "Pretreatment of Lignocellulosic Wastes to Improve Ethanol and Biogas Production: a Review", International Journal of Molecular Sciences, vol. 9, No. 9, Sep. 2008, pp. 1621-1651.

Kumakura et al., "Radiation Degradation and the Subsequent Enzymatic Hydrolysis of Waste Papers", Biotechnology and Bioengineering, vol. 24, No. 4, 1982, pp. 991-997.

Khan et al., "Effect of Electron-Beam Irradiation Pretreatment on the Enzymatic Hydrolysis of Softwood", Biotechnology and Bioengineering, vol. 28, No. 9, 1986, pp. 1449-1453.

Khan et al., "Electron Beam Irradiation Pretreatment and Enzymatic Saccharification of Used Newsprint and Paper Mill Wastes", International Journal of Radiation Applications and Instrumentation, Part C, Radiation Physics and Chemistry, Pergamon, vol. 29, No. 2, Jan. 1, 1987, pp. 117-120.

ISR and Written Opinion for PCT/US2010/023957, EPO as ISA, dated Jan. 3, 2011, 19 pages.

Invitation to Pay Applicable Fees for corresponding PCT application PCT/US2010/023957, EPO as ISA, dated Nov. 5, 2010, 9 pages.

Dziedziela, W. and Kotynska D., "Functional Groups in y-Irradiated Cellulose", Radiat. Phys. Chem., vol. 23(6), 1984, pp. 723-725.

MSDS, "Hydrogen Peroxide, 30%", Thermo Fisher Scientific Material Safety Data Sheet, Aug. 25, 2011, 9 pages.

* cited by examiner

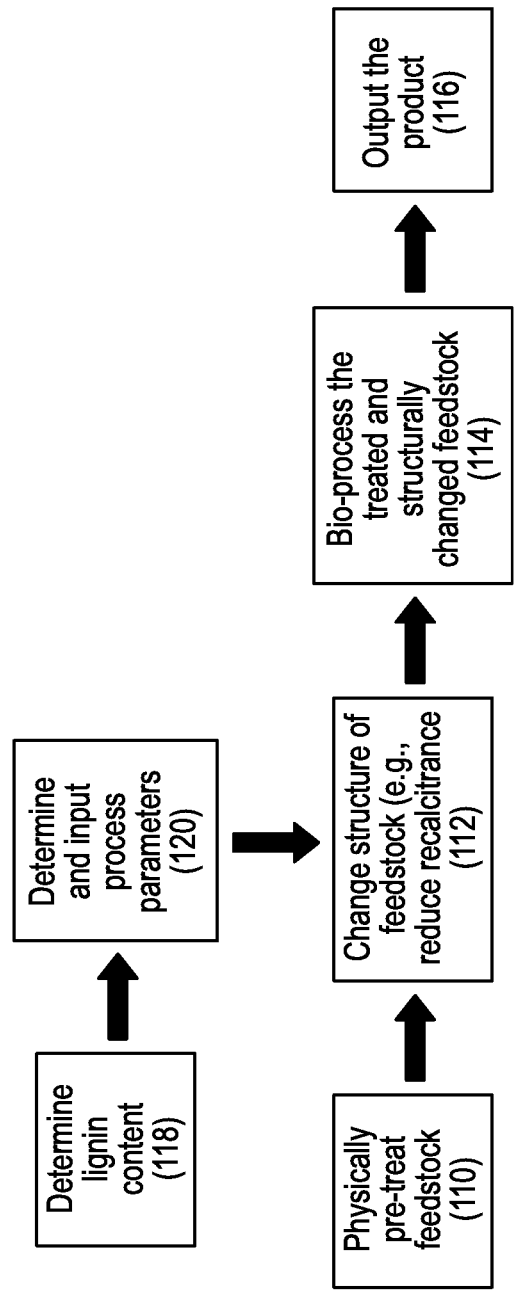

PROCESSING FACILITY

RELATED APPLICATIONS

This application is a continuation application of U.S. Application Ser. No. 151/141,281, filed Apr. 28, 2016, which is a continuation application of U.S. application Ser. No. 14/887,153, filed Oct. 19, 2015, which is a continuation application of U.S. application Ser. No. 14/494,815, filed Sep. 24, 2014, now U.S. Pat. No. 9,181,567, granted on Nov. 10, 2015, which is a continuation application of U.S. application Ser. No. 13/786,920, filed Mar. 6, 2013, now U.S. Pat. No. 8,877,467, granted on Nov. 4, 2014, which is a continuation application of U.S. application Ser. No. 12/704,519, filed Feb. 11, 2010, now U.S. Pat. No. 8,415,122, granted on Apr. 9, 2013, which claims priority to U.S. Provisional Application Ser. No. 61/151,724, filed Feb. 11, 2009. The complete disclosures of these applications are hereby incorporated by reference herein.

BACKGROUND

Various carbohydrates, such as cellulosic and lignocellulosic materials, e.g., in fibrous form, are produced, processed, and used in large quantities in a number of applications. Often such materials are used once, and then discarded as waste, or are simply considered to be waste materials, e.g., sewage, bagasse, sawdust, and stover.

Various cellulosic and lignocellulosic materials, their uses, and applications have been described in U.S. Pat. Nos. 7,307,108, 7,074,918, 6,448,307, 6,258,876, 6,207,729, 5,973,035 and 5,952,105; and in various patent applications, including "FIBROUS MATERIALS AND COMPOSITES," PCT/US2006/010648, filed on Mar. 23, 2006, AND "FIBROUS MATERIALS AND COMPOSITES," U.S. Patent Application Publication No. 2007/0045456.

SUMMARY

Generally, this invention relates to processes for manufacturing an intermediate or a product, e.g., energy, a fuel such as ethanol, a food or a material, from a plurality of different carbon-containing feedstocks and/or from a feedstock having a variable composition. The carbon-containing feedstock may include, for example, carbohydrate-containing materials (e.g., starchy materials and/or cellulosic or lignocellulosic materials), and may in some cases be a waste material having an unpredictable or variable composition.

The processes disclosed herein, alone or in combination, change the molecular structure and/or recalcitrance level of the feedstock(s), allowing a desired product to be obtained from the feedstock in an economically feasible manner. The inventors have found that the amount of change to the structure and/or recalcitrance level of the feedstock required to produce a product varies as a function of the lignin content of the feedstock. For example, the change in recalcitrance needed can be directly proportional to the lignin content. Accordingly, the methods disclosed herein involve adjusting the process type or one or more process parameters used to manufacture the product to compensate for changes in the lignin content of the feedstock that is being used, e.g., applying a higher or lower dose or dose rate during the pretreatment process used.

Many of the methods described herein can provide cellulosic and/or lignocellulosic materials that have, for example, a lower recalcitrance level, a lower molecular weight, a different level of functionalization and/or crystallinity relative to a native material. Many of the methods provide materials that can be more readily utilized by a variety of microorganisms, such as one or more homoacetogens or heteroacetogens (with or without enzymatic hydrolysis assistance) to produce useful products, such as energy, fuels, foods and materials. Specific examples of products include, but are not limited to, hydrogen, alcohols (e.g., monohydric alcohols or dihydric alcohols, such as ethanol, n-propanol or n-butanol), sugars, biodiesel, organic acids (e.g., acetic acid and/or lactic acid), hydrocarbons, co-products (e.g., proteins, such as cellulolytic proteins (enzymes) or single cell proteins), and mixtures of any of these. Other examples include carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones, aldehydes, alpha, beta unsaturated acids, such as acrylic acid and olefins, such as ethylene. Other alcohols and alcohol derivatives include propanol, propylene glycol, 1,4-butanediol, 1,3-propanediol, methyl or ethyl esters of any of these alcohols. Other products include methyl acrylate, methylmethacrylate, lactic acid, propionic acid, butyric acid, succinic acid, 3-hydroxypropionic acid, a salt of any of the acids and a mixture of any of the acids and respective salts.

Other products and intermediates, including food and pharmaceutical products, are described in U.S. Provisional Application Ser. No. 61/139,453, the full disclosure of which is hereby incorporated by reference herein in its entirety.

Many of the products obtained by the methods disclosed herein, such as ethanol or n-butanol, can be utilized directly as a fuel or as a blend with other components, such as gasoline, for powering cars, trucks, tractors, ships or trains, e.g., as an internal combustion fuel or as a fuel cell feedstock. Other products described herein (e.g., organic acids, such as acetic acid and/or lactic acid) can be converted to other moieties (e.g., esters or anhydrides) that can be converted and utilized as a fuel. Many of the products obtained can also be utilized to power aircraft, such as planes, e.g., having jet engines, or helicopters. In addition, the products described herein can be utilized for electrical power generation, e.g., in a conventional steam generating plant or in a fuel cell plant.

In one aspect, the invention features a method of making a product comprising determining the lignin content of a biomass feedstock; treating the biomass feedstock material with a physical treatment; setting a process parameter of the process based on the lignin content; and converting at least a portion of the treated biomass feedstock, utilizing a microorganism, to produce a product or intermediate, such as energy, fuels, foods or materials.

The physical treatment can be, for example, selected from the group consisting of mechanical treatment, radiation, sonication, pyrolysis, oxidation, steam explosion, chemical treatment, and combinations thereof. Chemical treatment may include the use of a single chemical or two or more chemicals. Mechanical treatments include, for example, cutting, milling, pressing, grinding, shearing and chopping. Milling may include, for example, ball milling, hammer milling, or other types of milling.

Some implementations include one or more of the following features. The physical treatment can comprise any one or more of the treatments listed above, applied alone or in any desired combination, and applied once or multiple times. In some cases, the physical treatment can comprise irradiating with ionizing radiation, alone or accompanied by mechanical treatment before and/or after irradiation. Irradiation can be performed, for example, with an electron beam.

The setting step can comprise setting the dosage of ionizing radiation to be delivered to the feedstock material. For example, a radiation dosage of 0.1 Mrad to 5.0 Mrad can be delivered per 1% by weight of lignin in the biomass feedstock, e.g., 0.25 Mrad to 4.0 Mrad or 0.3 Mrad to 3.5 Mrad.

The intermediate or product can be, for example, any one or more of the products listed herein. In some cases, the product can be energy or a fuel, for example biodiesel or an alcohol such as ethanol or methanol. The intermediate or product can also be, e.g., a carboxylic acid, an ester of a carboxylic acid, a salt of a carboxylic acid, or a mixture thereof.

The method can further include repeating the determining, treating and setting steps with a second feedstock.

In another aspect, the invention features a method of making a product or intermediate, the method including providing a cellulosic or lignocellulosic material having a plurality of pendent carboxylic acid groups, mixing the material in a fluid that includes water to provide a dispersion that has a first pH, and adding base to the dispersion to increase its pH to a second pH higher than the first pH. The first pH can be, for example, between 2.5 and 4.5, e.g., between 3 and 4.25. The second pH can be, for example, between about 5 and 7, e.g., between about 5.5 and 6.5.

Some implementations include one or more of the following features. The method can further include adding a cellulase to the dispersion to saccharify the cellulosic or lignocellulosic material. The method can further include contacting the saccharified material with a microorganism.

In some implementations, one or more components of the processing equipment, for example the mechanical treatment equipment, chemical (e.g., acid or base) treatment equipment, irradiating equipment, sonicating, pyrolyzing, oxidizing, steam exploding, saccharifying, and/or fermenting equipment, or any of the other equipment described herein, may be portable, e.g., in the manner of the mobile processing equipment described in U.S. patent application Ser. No. 12/374,549, and Published International Application No. WO 2008/011598, the full disclosures of which are incorporated herein by reference.

Changing a molecular structure of a material, as used herein, means to change the chemical bonding arrangement or conformation of the structure. For example, the change in the molecular structure can include changing the supramolecular structure of the material, oxidation of the material, changing an average molecular weight, changing an average crystallinity, changing a surface area, changing a degree of polymerization, changing a porosity, changing a degree of branching, grafting on other materials, changing a crystalline domain size, or changing an overall domain size. A change in molecular structure may be effected using any one or more of the physical treatments described herein, alone or in any combination, applied once or repeatedly.

All publications, patent applications, patents, and other references mentioned herein or attached hereto are incorporated by reference in their entirety for all that they contain.

DESCRIPTION OF THE DRAWINGS

FIG. 2 is a schematic diagram illustrating a process for making ethanol.

DETAILED DESCRIPTION

Figure 1:
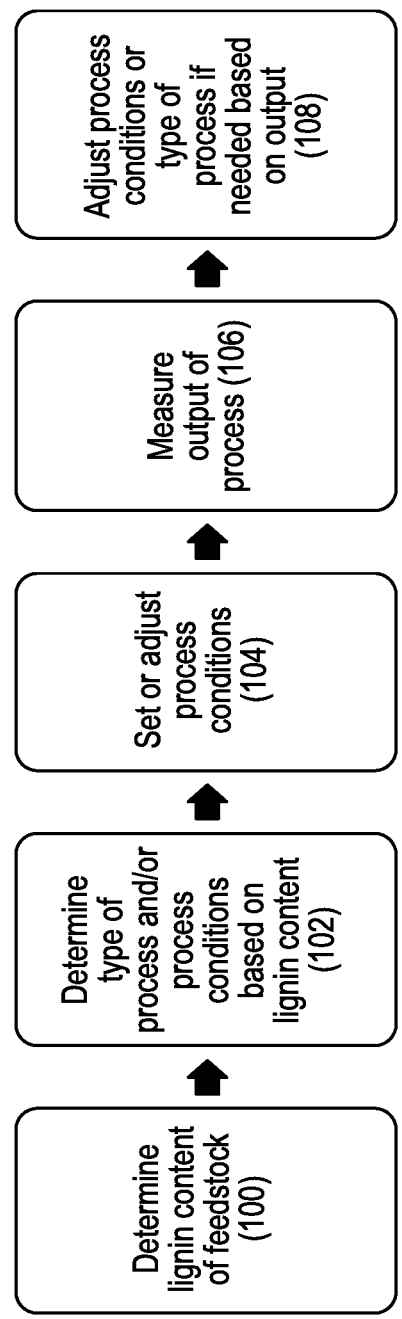
FIG. 1 is a flow diagram illustrating a process for making a product from a carbon-containing feedstock having a variable lignin content.

Biomass feedstocks (e.g., plant biomass, animal biomass, and municipal waste biomass) can be processed to a lower level of recalcitrance (if necessary) and converted into useful products such as those listed by way of example herein. Systems and processes are described herein that use readily abundant but often difficult to process materials, such as cellulosic or lignocellulosic materials which would otherwise be waste, e.g., crop residues and waste paper.

Generally, a manufacturing plant utilizing the processes described herein will obtain a variety of different feedstocks in the course of its operation. Some feedstocks may be relatively homogeneous in composition, for example a shipment of corn cobs, while other feedstocks may be of variable composition, for example municipal waste, e.g., various waste paper streams.

Feedstocks can include, for example, paper, paper products, wood, wood-related materials, particle board, grasses, rice hulls, bagasse, cotton, jute, hemp, flax, bamboo, sisal, abaca, straw, corn cobs, coconut hair, algae, seaweed, altered celluloses, e.g., cellulose acetate, regenerated cellulose, and the like, or mixtures of any of these.

In some cases the biomass is a microbial material. Microbial sources include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

To allow the manufacturing plant to utilize these different types of feedstocks to produce one or more desired products, the manufacturing process is adjustable to compensate for variations and/or within the feedstocks, e.g., to compensate for variations in the lignin content of the different feedstocks.

Many of the processes described herein can effectively lower the recalcitrance level of the feedstock, making it easier to process, such as by bioprocessing (e.g., with any microorganism described herein, such as a homoacetogen or a heteroacetogen, and/or any enzyme described herein), thermal processing (e.g., gasification or pyrolysis) or chemical methods (e.g., acid hydrolysis or oxidation). Biomass feedstock can be treated or processed using one or more of any of the methods described herein, such as mechanical treatment, chemical treatment, radiation, sonication, oxidation, pyrolysis or steam explosion. The various treatment systems and methods can be used in combinations of two, three, or even four or more of these technologies or others described herein and elsewhere.

Figure 1A:
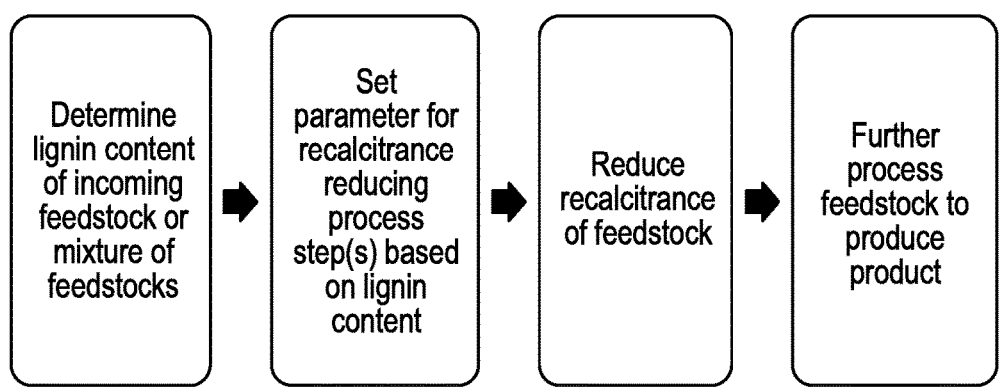
FIG. 1A is a flow diagram illustrating steps of the process shown in FIG. 1 according to one implementation.

As shown in FIG. 1, in some implementations the lignin content of the incoming feedstock is determined (step 100), and then, based on the lignin content, the type of physical treatment(s) (e.g., mechanical treatment, radiation, sonication, etc.) and/or one or more processing conditions required to obtain the desired product are determined (step 102). If the feedstock has a relatively high level of variability, e.g., municipal waste, a number of samples may be taken and the average lignin content calculated. In some cases, the feedstock may be pre-treated to homogenize it prior to lignin content measurement, for example by grinding or pulverizing, e.g., freeze-grinding (e.g., as disclosed in U.S. Provisional Application No. 61/081,709, filed Jul. 17, 2008, the full disclosure of which is incorporated herein by reference). In some cases, e.g., as shown in FIG. 1A, two or more incoming feedstocks can be mixed together to form a combined feedstock, and the lignin content of the combined feedstock can be measured.

Methods for preparing samples and determining lignin content are disclosed in Department of Energy (DOE) test procedures NREL/TP-510-42618 (Revised April 2008), NREL/TP-510-42619 (Revised January 2008), and NREL/TP-510-42620 (Revised January 2008).

Once the lignin content has been determined, it can be used, e.g., based on empirically determined relationships between lignin content and recalcitrance, to determine the processing conditions, which are then input to the processing equipment (step 104). For example, as shown in FIG. 1A, the parameters may be those used in one or more recalcitrance-reducing process steps that will change the structure and/or reduce the recalcitrance of the feedstock, as will be described in further detail below.

If desired, the output of the process can be monitored (step 106, FIG. 1), and the process parameters adjusted based on these measurements (step 108, FIG. 1). For example, the volume, purity, or other characteristics of the output can be measured. The output may be the final product, or may be an intermediate product, such as a lignocellulosic or cellulosic material having reduced recalcitrance.

Referring now to FIG. 2, in one example the methodology discussed above can be integrated into a process for manufacturing a product, e.g., energy, fuel, food or material, for example an alcohol such as ethanol. Such a process can include, for example, mechanically treating the feedstock (step 110), before and/or after this treatment, treating the feedstock with another physical treatment, for example irradiation, to further reduce its recalcitrance (step 112), and then processing the treated feedstock to produce a desired product (step 114) which is output, e.g., by distillation (step 116). The individual steps of this process will be described in detail below. The steps of measuring lignin content (step 118) and setting or adjusting process parameters (step 120) can be performed at various stages of the process, for example just prior to the process step(s) used to change the structure of the feedstock, as shown.

Figure 3:
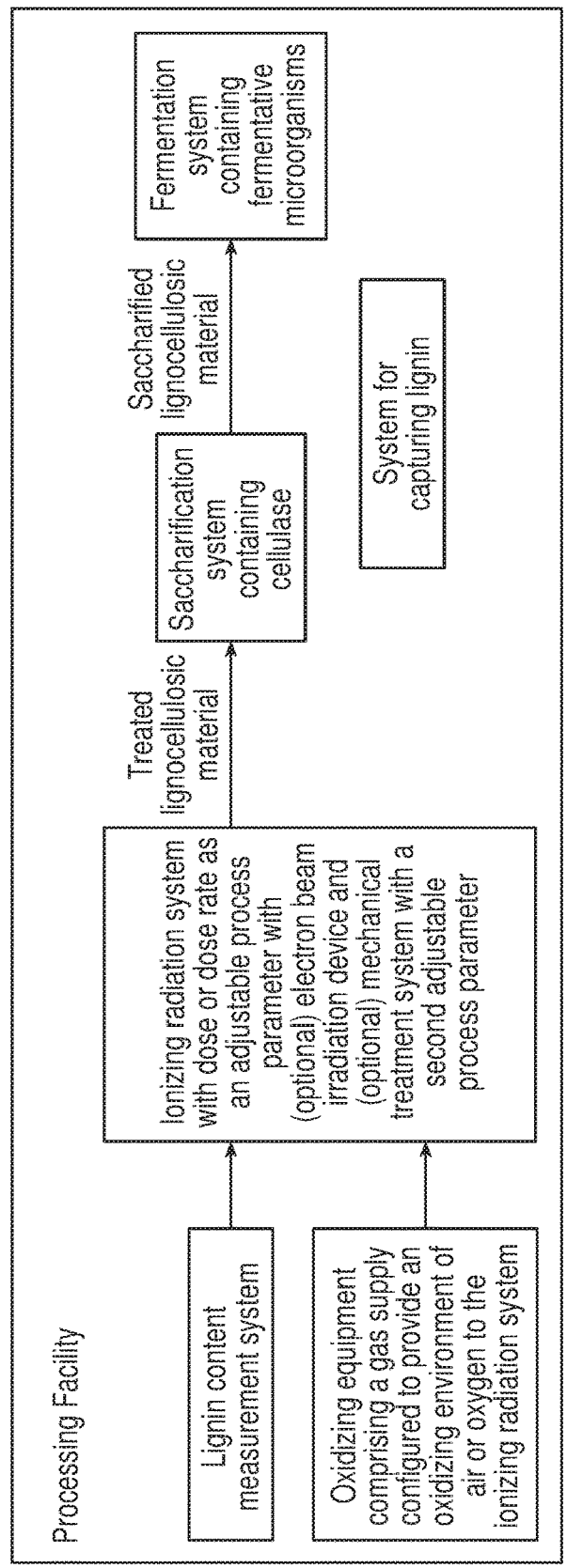
FIG. 3 is a schematic of a processing facility to process a lignocellulosic material.

FIG. 3 shows a schematic of a processing facility to process a lignocellulosic material to a product.

Biomass Materials

The biomass can be, e.g., a cellulosic or lignocellulosic material. Such materials include paper and paper products (e.g., polycoated paper and Kraft paper), wood, wood-related materials, e.g., particle board, grasses, rice hulls, bagasse, jute, hemp, flax, bamboo, sisal, abaca, straw, corn cobs, coconut hair; and materials high in α-cellulose content, e.g., cotton. Feedstocks can be obtained from virgin scrap textile materials, e.g., remnants, post consumer waste, e.g., rags. When paper products are used they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Biomass feedstocks can also be obtained or derived from human (e.g., sewage), animal or plant wastes. Additional cellulosic and lignocellulosic materials have been described in U.S. Pat. Nos. 6,448,307, 6,258,876, 6,207,729, 5,973,035 and 5,952,105.

In some embodiments, the biomass material includes a carbohydrate that is or includes a material having one or more β-1,4-linkages and having a number average molecular weight between about 3,000 and 50,000. Such a carbohydrate is or includes cellulose (I), which is derived from (β-glucose 1) through condensation of β(1,4)-glycosidic bonds. This linkage contrasts itself with that for α(1,4)-glycosidic bonds present in starch and other carbohydrates.

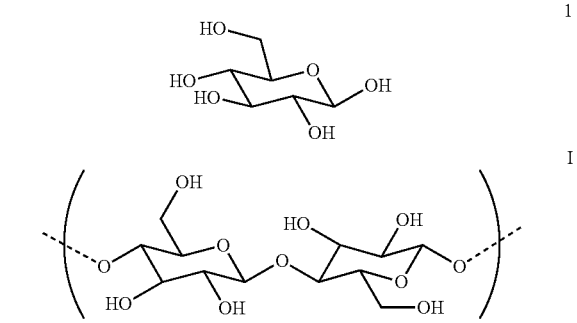

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. In particular embodiments, the starchy material is derived from corn. Various corn starches and derivatives are described in "Corn Starch," Corn Refiners Association (11$^{th}$ Edition, 2006).

In some cases the biomass is a microbial material. Microbial sources include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Examples of Other Blends

Blends of the biomass feedstock with other materials, e.g., carbon-containing materials such as pre-coal or coal, e.g., peat, lignite, sub-bituminous, bituminous and anthracite, oil sand, oil shale can also be utilized. In addition, blends of any biomass materials described herein with other carbon-containing material can be utilized for making any of the products described herein, such as ethanol, acetic acid or ethyl acetate.

Physical Treatment

Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment methods is used, the methods can be applied at the same time or at different times. Other processes that change a molecular structure of a biomass feedstock may also be used, alone or in combination with the processes disclosed herein.

One or more of the treatment processes described below may be included in the recalcitrance reducing operating unit discussed above. Alternatively, or in addition, other processes for reducing recalcitrance may be included.

Mechanical Treatments

In some cases, methods can include mechanically treating the biomass feedstock. Mechanical treatments include, for example, cutting, milling, pressing, grinding, shearing and chopping. Milling may include, for example, ball milling, hammer milling, rotor/stator dry or wet milling, or other types of milling. Other mechanical treatments include, e.g., stone grinding, cracking, mechanical ripping or tearing, pin grinding or air attrition milling.

Mechanical treatment can be advantageous for "opening up," "stressing," breaking and shattering the cellulosic or lignocellulosic materials, making the cellulose of the materials more susceptible to chain scission and/or reduction of crystallinity. The open materials can also be more susceptible to oxidation when irradiated.

In some cases, the mechanical treatment may include an initial preparation of the feedstock as received, e.g., size reduction of materials, such as by cutting, grinding, shearing, pulverizing or chopping. For example, in some cases, loose feedstock (e.g., recycled paper, starchy materials, or switchgrass) is prepared by shearing or shredding.

Alternatively, or in addition, the feedstock material can be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the molecular structure of the material by mechanical treatment.

In some embodiments, the feedstock material is in the form of a fibrous material, and mechanical treatment includes shearing to expose fibers of the fibrous material. Shearing can be performed, for example, using a rotary knife cutter. Other methods of mechanically treating the feedstock include, for example, milling or grinding. Milling may be performed using, for example, a hammer mill, ball mill, colloid mill, conical or cone mill, disk mill, edge mill, Wiley mill or grist mill. Grinding may be performed using, for example, a stone grinder, pin grinder, coffee grinder, or burr grinder. Grinding may be provided, for example, by a reciprocating pin or other element, as is the case in a pin mill. Other mechanical treatment methods include mechanical ripping or tearing, other methods that apply pressure to the fibers, and air attrition milling. Suitable mechanical treatments further include any other technique that changes the molecular structure of the feedstock.

If desired, the mechanically treated material can be passed through a screen, e.g., having an average opening size of 1.59 mm or less (1/16 inch, 0.0625 inch). In some embodiments, shearing, or other mechanical treatment, and screening are performed concurrently. For example, a rotary knife cutter can be used to concurrently shear the and screen the feedstock. The feedstock is sheared between stationary blades and rotating blades to provide a sheared material that passes through a screen, and is captured in a bin. The bin can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source is utilized to maintain the bin below nominal atmospheric pressure.

The cellulosic or lignocellulosic material can be mechanically treated in a dry state (e.g., having little or no free water on its surface), a hydrated state (e.g., having up to ten percent by weight absorbed water), or in a wet state, e.g., having between about 10 percent and about 75 percent by weight water. The fiber source can even be mechanically treated while partially or fully submerged under a liquid, such as water, ethanol or isopropanol.

The cellulosic or lignocellulosic material can also be mechanically treated under a gas (such as a stream or atmosphere of gas other than air), e.g., oxygen or nitrogen, or steam.

If desired, lignin can be removed from any of the fibrous materials that include lignin. Also, to aid in the breakdown of the materials that include cellulose, the material can be treated prior to or during mechanical treatment or irradiation with heat, a chemical (e.g., mineral acid, base or a strong oxidizer such as sodium hypochlorite) and/or an enzyme. For example, grinding can be performed in the presence of an acid.

Mechanical treatment systems can be configured to produce streams with specific characteristics such as, for example, specific maximum sizes, specific length-to-width, or specific surface areas ratios. Mechanical treatment can increase the rate of reactions or reduce the processing time required by opening up the materials and making them more accessible to processes and/or reagents, such as reagents in a solution. The bulk density of feedstocks can also be controlled using mechanical treatment. For example, in some embodiments, after mechanical treatment the material has a bulk density of less than 0.25 g/cm$^3$, e.g., 0.20 g/cm$^3$, 0.15 g/cm$^3$, 0.10 g/cm$^3$, 0.05 g/cm$^3$ or less, e.g., 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

If the feedstock is a fibrous material the fibers of the mechanically treated material can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (e.g., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

If the feedstock is a fibrous material the average length-to-diameter ratio of fibers of the mechanically treated material can be, e.g., greater than 8/1, e.g., greater than 10/1, greater than 15/1, greater than 20/1, greater than 25/1, or greater than 50/1. An average fiber length of the mechanically treated material can be, e.g., between about 0.5 mm and 2.5 mm, e.g., between about 0.75 mm and 1.0 mm, and an average width (e.g., diameter) of the second fibrous material 14 can be, e.g., between about 5 µm and 50 µm, e.g., between about 10 µm and 30 µm.

In some embodiments, if the feedstock is a fibrous material the standard deviation of the fiber length of the mechanically treated material can be less than 60 percent of an average fiber length of the mechanically treated material, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the mechanically treated material is greater than 0.1 m$^2$/g, e.g., greater than 0.25 m$^2$/g, greater than 0.5 m$^2$/g, greater than 1.0 m$^2$/g, greater than 1.5 m$^2$/g, greater than 1.75 m$^2$/g, greater than 5.0 m$^2$/g, greater than 10 m$^2$/g, greater than 25 m$^2$/g, greater than 35 m$^2$/g, greater than 50 m$^2$/g, greater than 60 m$^2$/g, greater than 75 m$^2$/g, greater than 100 m$^2$/g, greater than 150 m$^2$/g, greater than 200 m$^2$/g, or even greater than 250 m$^2$/g.

A porosity of the mechanically treated material can be, e.g., greater than 20 percent, greater than 25 percent, greater than 35 percent, greater than 50 percent, greater than 60 percent, greater than 70 percent, greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some situations, it can be desirable to prepare a low bulk density material, densify the material (e.g., to make it easier and less costly to transport to another site), and then revert the material to a lower bulk density state. Densified materials can be processed by any of the methods described herein, or any material processed by any of the methods described herein can be subsequently densified, e.g., as disclosed in WO 2008/073186.

Radiation Treatment

One or more radiation processing sequences can be used to process the feedstock, and to provide a structurally modified material which functions as input to further processing steps and/or sequences. Irradiation can, for example, reduce the molecular weight and/or crystallinity of feedstock. In some embodiments, energy deposited in a material that releases an electron from its atomic orbital is used to irradiate the materials. The radiation may be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized. In another approach, electromagnetic radiation (e.g., produced using electron beam emitters) can be used to irradiate the feedstock. The doses applied depend on the desired effect and the particular feedstock. For example, high doses of radiation can break chemical bonds within feedstock components. In some instances when chain scission is desirable and/or polymer chain functionalization is desirable, particles heavier than electrons, such as protons, helium nuclei, argon ions, silicon ions, neon ions, carbon ions, phoshorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized.

In one method, a first material that is or includes cellulose having a first number average molecular weight ($M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material that includes cellulose having a second number average molecular weight ($M_{N2}$) lower than the first number average molecular weight. The second material (or the first and second material) can be combined with a microorganism (with or without enzyme treatment) that can utilize the second and/or first material or its constituent sugars or lignin to produce a fuel or other useful product that is or includes hydrogen, an alcohol (e.g., ethanol or butanol, such as n-, sec- or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing a microorganism and/or an enzyme. These properties make the second material more susceptible to chemical, enzymatic and/or biological attack relative to the first material, which can greatly improve the production rate and/or production level of a desired product, e.g., ethanol. Radiation can also sterilize the materials, or any media needed to bioprocess the material.

In some embodiments, the second number average molecular weight ($M_{N2}$) is lower than the first number average molecular weight ($M_{N1}$) by more than about 10 percent, e.g., 15, 20, 25, 30, 35, 40, 50 percent, 60 percent, or even more than about 75 percent.

In some instances, the second material has cellulose that has as crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the carbon-containing material via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part due to their acidic nature. When particles are utilized, the particles can have the mass of a resting electron, or greater, e.g., 500, 1000, 1500, 2000, 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodatron® system, while DC type accelerators are available from RDI, now IBA Industrial, such as the Dynamitron®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy" Columbus-Ohio, ICRU-IAEA Meeting, 18-20 Mar. 2006, Iwata, Y. et al., "Alternating-Phase-Focused IH-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria.

Gamma radiation has the advantage of a significant penetration depth into a variety of materials. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. The level of depolymerization of the feedstock depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Ion Particle Beams

Particles heavier than electrons can be utilized to irradiate materials, such as carbohydrates or materials that include carbohydrates, e.g., cellulosic materials, lignocellulosic materials, starchy materials, or mixtures of any of these and others described herein. For example, protons, helium nuclei, argon ions, silicon ions, neon ions carbon ions, phosphorus ions, oxygen ions or nitrogen ions can be utilized. In some embodiments, particles heavier than electrons can induce higher amounts of chain scission (relative to lighter particles). In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

In certain embodiments, ion beams used to irradiate carbon-containing materials, e.g., biomass materials, can include more than one type of ion. For example, ion beams can include mixtures of two or more (e.g., three, four or more) different types of ions. Exemplary mixtures can include carbon ions and protons, carbon ions and oxygen ions, nitrogen ions and protons, and iron ions and protons. More generally, mixtures of any of the ions discussed above (or any other ions) can be used to form irradiating ion beams. In particular, mixtures of relatively light and relatively heavier ions can be used in a single ion beam.

In some embodiments, ion beams for irradiating materials include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to materials, initiating and sustaining cationic ring-opening chain scission reactions in an oxidative environment.

In certain embodiments, ion beams for irradiating materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to materials, causing anionic ring-opening chain scission reactions in a reducing environment.

In some embodiments, beams for irradiating materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

In certain embodiments, ion beams used to irradiate materials include singly-charged ions such as one or more of $H^+$, $H^-$, $He^+$, $Ne^+$, $Ar^+$, $C^+$, $C^-$, $O^+$, $O^-$, $N^+$, $N^-$, $Si^+$, $Si^-$, $P^+$, $P^-$, $Na^+$, $Ca^+$, and $Fe^+$. In some embodiments, ion beams can include multiply-charged ions such as one or more of $C^{2+}$, $C^{3+}$, $C^{4+}$, $N^{3+}$, $N^{5+}$, $N^{3-}$, $O^{2+}$, $O^{2-}$, $O_2^{2-}$, $Si^{2+}$, $Si^{4+}$, $Si^{2-}$, and $Si^{4-}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ hz, greater than $10^{17}$ hz, $10^{18}$, $10^{19}$, $10^{20}$, or even greater than $10^{21}$ hz. In some embodiments, the electromagnetic radiation has a frequency of between $10^{18}$ and $10^{22}$ hz, e.g., between $10^{19}$ to $10^{21}$ hz.

Doses

The dose of radiation will depend on the lignin content of the feedstock. For example, in some cases 0.1 Mrad to 5.0 Mrad is delivered per 1% by weight of lignin in the biomass feedstock, e.g. 0.25 Mrad to 4.0 Mrad, or 0.3 Mrad to 3.5 Mrad per 1%.

In some embodiments, the irradiating (with any radiation source or a combination of sources) is performed until the material receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad.

In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light.

Sonication

One or more sonication processing sequences can be used to process materials from a wide variety of different sources to extract useful substances from the materials, and to provide partially degraded organic material (when organic materials are employed) which functions as input to further processing steps and/or sequences. Sonication can reduce the molecular weight and/or crystallinity of the materials, such as one or more of any of the materials described herein, e.g., one or more carbohydrate sources, such as cellulosic or lignocellulosic materials, or starchy materials. As discussed above with regard to radiation, the process parameters used for sonication will vary depending on the lignin content of the feedstock. For example, feedstocks with higher lignin levels generally require a higher residence time and/or energy level, resulting in a higher total energy delivered to the feedstock.

In one method, a first material that includes cellulose having a first number average molecular weight ($M_{N1}$) is dispersed in a medium, such as water, and sonicated and/or otherwise cavitated, to provide a second material that includes cellulose having a second number average molecular weight ($M_{N2}$) lower than the first number average molecular weight. The second material (or the first and second material in certain embodiments) can be combined with a microorganism (with or without enzyme treatment) that can utilize the second and/or first material to produce a fuel that is or includes hydrogen, an alcohol, an organic acid, a hydrocarbon or mixtures of any of these.

Since the second material has cellulose having a reduced molecular weight relative to the first material, and in some instances, a reduced crystallinity as well, the second material is generally more dispersible, swellable, and/or soluble in a solution containing the microorganism, e.g., at a concentration of greater than $10^6$ microorganisms/mL. These properties make the second material more susceptible to chemical, enzymatic, and/or microbial attack relative to the first material, which can greatly improve the production rate and/or production level of a desired product, e.g., ethanol. Sonication can also sterilize the materials, but should not be used while the microorganisms are supposed to be alive.

In some embodiments, the second number average molecular weight ($M_{N2}$) is lower than the first number average molecular weight ($M_{N1}$) by more than about 10 percent, e.g., 15, 20, 25, 30, 35, 40, 50 percent, 60 percent, or even more than about 75 percent.

In some instances, the second material has cellulose that has as crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Pyrolysis

One or more pyrolysis processing sequences can be used to process carbon-containing materials from a wide variety of different sources to extract useful substances from the materials, and to provide partially degraded materials which function as input to further processing steps and/or sequences. Feedstocks with higher lignin levels generally require a higher temperature, longer residence time, and/or introduction of higher levels of oxygen during pyrolysis.

In one example, a first material that includes cellulose having a first number average molecular weight ($M_{N1}$) is pyrolyzed, e.g., by heating the first material in a tube furnace (in the presence or absence of oxygen), to provide a second material that includes cellulose having a second number average molecular weight ($M_{N2}$) lower than the first number average molecular weight. The second material (or the first and second material in certain embodiments) is/are combined with a microorganism (with or without acid or enzymatic hydrolysis) that can utilize the second and/or first material to produce a fuel that is or includes hydrogen, an alcohol (e.g., ethanol or butanol, such as n-, sec or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing the microorganism, e.g., at a concentration of greater than $10^6$ microorganisms/mL. These properties make the second material more susceptible to chemical, enzymatic and/or microbial attack relative to the first material, which can greatly improve the production rate and/or production level of a desired product, e.g., ethanol. Pyrolysis can also sterilize the first and second materials.

In some embodiments, the second number average molecular weight ($M_{N2}$) is lower than the first number average molecular weight ($M_{N1}$) by more than about 10 percent, e.g., 15, 20, 25, 30, 35, 40, 50 percent, 60 percent, or even more than about 75 percent.

In some instances, the second material has cellulose that has as crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the materials susceptibility to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, which can increase its hydrophilicity.

In some embodiments, the pyrolysis of the materials is continuous. In other embodiments, the material is pyrolyzed for a pre-determined time, and then allowed to cool for a second pre-determined time before pyrolyzing again.

Oxidation

One or more oxidative processing sequences can be used to process carbon-containing materials from a wide variety of different sources to extract useful substances from the materials, and to provide partially degraded and/or altered material which functions as input to further processing steps and/or sequences. The oxidation conditions will vary depending on the lignin content of the feedstock, with a higher degree of oxidation generally being desired for higher lignin content feedstocks.

In one method, a first material that includes cellulose having a first number average molecular weight ($M_{N1}$) and having a first oxygen content ($O_1$) is oxidized, e.g., by heating the first material in a stream of air or oxygen-enriched air, to provide a second material that includes cellulose having a second number average molecular weight ($M_{N2}$) and having a second oxygen content ($O_2$) higher than the first oxygen content ($O_1$).

Such materials can also be combined with a solid and/or a liquid. The liquid and/or solid can include a microorganism, e.g., a bacterium, and/or an enzyme. For example, the bacterium and/or enzyme can work on the cellulosic or lignocellulosic material to produce a fuel, such as ethanol, or a coproduct, such as a protein. Fuels and coproducts are described in FIBROUS MATERIALS AND COMPOSITES," U.S. Ser. No. 11/453,951, filed Jun. 15, 2006. The entire contents of each of the foregoing applications are incorporated herein by reference.

In some embodiments, the second number average molecular weight is not more 97 percent lower than the first number average molecular weight, e.g., not more than 95 percent, 90, 85, 80, 75, 70, 65, 60, 55, 50, 45, 40, 30, 20, 12.5, 10.0, 7.5, 5.0, 4.0, 3.0, 2.5, 2.0 or not more than 1.0 percent lower than the first number average molecular weight. The amount of reduction of molecular weight will depend upon the application. For example, in some preferred embodiments that provide composites, the second number average molecular weight is substantially the same as the first number average molecular weight. In other applications, such as making ethanol or another fuel or coproduct, a higher amount of molecular weight reduction is generally preferred.

In some embodiments in which the materials are used to make a fuel or a coproduct, the starting number average molecular weight (prior to oxidation) is from about 200,000 to about 3,200,000, e.g., from about 250,000 to about 1,000,000 or from about 250,000 to about 700,000, and the number average molecular weight after oxidation is from about 50,000 to about 200,000, e.g., from about 60,000 to about 150,000 or from about 70,000 to about 125,000. However, in some embodiments, e.g., after extensive oxidation, it is possible to have a number average molecular weight of less than about 10,000 or even less than about 5,000.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the first oxygen content of the first material. Oxygen content is measured by elemental analysis by pyrolyzing a sample in a furnace operating at 1300° C. or higher. A suitable elemental analyzer is the LECO CHNS-932 analyzer with a VTF-900 high temperature pyrolysis furnace.

Generally, oxidation of a material occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Some oxidative methods of reducing recalcitrance in a biomass feedstock employ Fenton or Fenten-type chemistry. Such methods are disclosed, for example, in U.S. Provisional Application No. 61/139,473, filed Dec. 19, 2008, the complete disclosure of which is incorporated herein by reference.

Exemplary oxidants include peroxides, such as hydrogen peroxide and benzoyl peroxide, persulfates, such as ammonium persulfate, activated forms of oxygen, such as ozone, permanganates, such as potassium permanganate, perchlorates, such as sodium perchlorate, and hypochlorites, such as sodium hypochlorite (household bleach).

In some situations, pH is maintained at or below about 5.5 during contact, such as between 1 and 5, between 2 and 5, between 2.5 and 5 or between about 3 and 5. Conditions can also include a contact period of between 2 and 12 hours, e.g., between 4 and 10 hours or between 5 and 8 hours. In some instances, conditions include not exceeding 300° C., e.g., not exceeding 250, 200, 150, 100 or 50° C. In special desirable instances, the temperature remains substantially ambient, e.g., at or about 20-25° C.

In some desirable embodiments, the one or more oxidants are applied to a first cellulosic or lignocellulosic material and the one or more compounds as a gas, such as by generating ozone in-situ by irradiating the first cellulosic or lignocellulosic material and the one or more compounds through air with a beam of particles, such as electrons.

In particular desirable embodiments, a first cellulosic or lignocellulosic material is firstly dispersed in water or an aqueous medium that includes the one or more compounds dispersed and/or dissolved therein, water is removed after a soak time (e.g., loose and free water is removed by filtration), and then the one or more oxidants are applied to the combination as a gas, such as by generating ozone in-situ by irradiating the first cellulosic or lignocellulosic and the one or more compounds through air with a beam of particles, such as electrons (e.g., each being accelerated by a potential difference of between 3 MeV and 10 MeV). Soaking can open up interior portions to oxidation.

In some embodiments, the mixture includes one or more compounds and one or more oxidants, and a mole ratio of the one or more compounds to the one or more oxidants is from about 1:1000 to about 1:25, such as from about 1:500 to about 1:25 or from about 1:100 to about 1:25.

In some desirable embodiments, the mixture further includes one or more hydroquinones, such as 2,5-dimethoxyhydroquinone (DMHQ) and/or one or more benzoquinones, such as 2,5-dimethoxy-1,4-benzoquinone (DMBQ), which can aid in electron transfer reactions.

In some desirable embodiments, the one or more oxidants are electrochemically-generated in-situ. For example, hydrogen peroxide and/or ozone can be electro-chemically produced within a contact or reaction vessel.

Other Processes to Solubilize, Reduce Recalcitrance or to Functionalize

Any of the processes of this paragraph can be used alone without any of the processes described herein, or in combination with any of the processes described herein (in any order): steam explosion, acid treatment (including concentrated and dilute acid treatment with mineral acids, such as sulfuric acid, hydrochloric acid and organic acids, such as trifluoroacetic acid), base treatment (e.g., treatment with lime or sodium hydroxide), UV treatment, screw extrusion treatment (see, e.g., U.S. Patent Application Ser. No. 61/073,530, filed Nov. 18, 2008, solvent treatment (e.g., treatment with ionic liquids) and freeze milling (see, e.g., U.S. Patent Application Ser. No. 61/081,709).

Thermochemical Conversion

A thermochemical conversion process includes changing molecular structures of carbon-containing material at elevated temperatures. Specific examples include gasification, pyrolysis, reformation, partial oxidation and mixtures of these (in any order).

Gasification converts carbon-containing materials into a synthesis gas (syngas), which can include methanol, carbon monoxide, carbon dioxide and hydrogen. Many microorganisms, such as acetogens or homoacetogens are capable of utilizing a syngas from the thermochemical conversion of biomass, to produce a product that includes an alcohol, a carboxylic acid, a salt of a carboxylic acid, a carboxylic acid ester or a mixture of any of these. Gasification of biomass (e.g., cellulosic or lignocellulosic materials), can be accomplished by a variety of techniques. For example, gasification can be accomplished utilizing staged steam reformation with a fluidized-bed reactor in which the carbonaceous material is first pyrolyzed in the absence of oxygen and then the pyrolysis vapors are reformed to synthesis gas with steam providing added hydrogen and oxygen. In such a technique, process heat comes from burning char. Another technique utilizes a screw auger reactor in which moisture (and oxygen) are introduced at the pyrolysis stage and the process heat is generated from burning some of the gas produced in the latter stage. Another technique utilizes entrained flow reformation in which both external steam and air are introduced in a single-stage gasification reactor. In partial oxidation gasification, pure oxygen is utilized with no steam.

Production of Fuels, Acids, Esters and/or Other Products

A typical biomass resource contains cellulose, hemicellulose, and lignin plus lesser amounts of proteins, extractables and minerals. After one or more of the processing steps discussed above have been performed on the biomass, the complex carbohydrates contained in the cellulose and hemicellulose fractions can be processed into fermentable sugars, optionally, along with acid or enzymatic hydrolysis. The sugars liberated can be converted into a variety of products, such as alcohols or organic acids. The product obtained depends upon the microorganism utilized and the conditions under which the bioprocessing occurs.

Thus, a biomass material can be treated to reduce its recalcitrance using any one or more of the treatment methods described herein, such as with one or more of radiation, sonication, pyrolysis, oxidation and steam explosion, and then at least a portion of the thus treated biomass can be converted utilizing a microorganism to produce a product that includes one or more of an alcohol, a carboxylic acid, a salt of a carboxylic acid, a carboxylic acid ester or a mixture of any of these. This product can then be acidified, esterified and/or hydrogenated, to form a final product, e.g., ethanol. In some cases, acetogens or homoacetogens, which are capable of utilizing a syngas from a thermochemical conversion process, can be utilized to enhance the efficiency of the conversion.

The carboxylic acid groups in these products generally lower the pH of the fermentation solution, tending to inhibit fermentation with some microorganisms, such *Pichia stipitis*. Accordingly, it is in some cases desirable to add base and/or a buffer, before or during fermentation, to bring up the pH of the solution. For example, sodium hydroxide or lime can be added to the fermentation medium to elevate the pH of the medium to range that is optimum for the microorganism utilized.

Suitable bioprocessing methods are disclosed, for example, in U.S. Provisional Application No. 61/147,377, filed Jan. 26, 2009, the complete disclosure of which is incorporated herein by reference.

Generally, various microorganisms can produce a number of useful products, such as a fuel, by operating on, e.g., fermenting the treated carbon-containing materials.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized. The microorganism can be an aerobe or an anaerobe. The microorganism can be a homofermentative microorganism (produces a single or a substantially single end product). The microorganism can be a homoacetogenic microorganism, a homolactic microorganism, a propionic acid bacterium, a butyric acid bacterium, a succinic acid bacterium or a 3-hydroxypropionic acid bacterium. The microorganism can be of a genus selected from the group *Clostridium, Lactobacillus, Moorella, Thermoanaerobacter, Proprionibacterium, Propionispera, Anaerobiospirillum*, and *Bacteroides*. In specific instances, the microorganism can be *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteroides amylophilus* or *Bacteroides ruminicola*. For example, the microorganism can be a recombinant microorganism engineered to produce a desired product, such as a recombinant *Escherichia coli* transformed with one or more genes capable of encoding proteins that direct the production of the desired product is used (see, e.g., U.S. Pat. No. 6,852,517, issued Feb. 8, 2005).

Bacteria that can ferment biomass to ethanol and other products include, e.g., *Zymomonas mobilis* and *Clostridium thermocellum* (Philippidis, 1996, supra). Leschine et al. (*International Journal of Systematic and Evolutionary Microbiology* 2002, 52, 1155-1160) isolated an anaerobic, mesophilic, cellulolytic bacterium from forest soil, *Clostridium phytofermentans* sp. nov., which converts cellulose to ethanol.

Fermentation of biomass to ethanol and other products may be carried out using certain types of thermophilic or genetically engineered microorganisms, such *Thermoanaerobacter* species, including *T. mathranii*, and yeast species such as *Pichia* species. An example of a strain of *T. mathranii* is A3M4 described in Sonne-Hansen et al. (*Applied Microbiology and Biotechnology* 1993, 38, 537-541) or Ahring et al. (*Arch. Microbiol.* 1997, 168, 114-119).

To aid in the breakdown of the materials that include the cellulose (treated by any method described herein or even untreated), one or more enzymes, e.g., a cellulolytic enzyme can be utilized. In some embodiments, the materials that include the cellulose are first treated with the enzyme, e.g., by combining the material and the enzyme in an aqueous solution. This material can then be combined with any microorganism described herein. In other embodiments, the materials that include the cellulose, the one or more enzymes and the microorganism are combined concurrently, e.g., by combining in an aqueous solution.

Fermentation is generally conducted in an aqueous growth medium, which can contain a nitrogen source or other nutrient source, e.g., urea, along with vitamins and trace minerals and metals. It is generally preferable that the growth medium be sterile, or at least have a low microbial load, e.g., bacterial count. Sterilization of the growth medium may be accomplished in any desired manner. However, in preferred implementations, sterilization is accomplished by irradiating the growth medium or the individual components of the growth medium prior to mixing. The dosage of radiation is generally as low as possible while still obtaining adequate results, in order to minimize energy consumption and resulting cost. For example, in many instances, the growth medium itself or components of the growth medium can be treated with a radiation dose of less than 5 Mrad, such as less than 4, 3, 2 or 1 Mrad. In specific instances, the growth medium is treated with a dose of between about 1 and 3 Mrad.

OTHER EMBODIMENTS

A number of embodiments have been described. Nevertheless, it will be understood that various modifications may be made without departing from the spirit and scope of the disclosure.

While it is possible to perform all the processes described herein all at one physical location, in some embodiments, the processes are completed at multiple sites, and/or may be performed during transport.

Lignin liberated in any process described herein can be captured and utilized. For example, the lignin can be used as captured as a plastic, or it can be synthetically upgraded to other plastics. In some instances, it can be utilized as an energy source, e.g., burned to provide heat. In some instances, it can also be converted to lignosulfonates, which can be utilized as binders, dispersants, emulsifiers or as sequestrants. The measurement of the lignin content of the starting feedstock can be used in process control in such lignin-capturing processes.

When used as a binder, the lignin or a lignosulfonate can, e.g., be utilized in coal briquettes, in ceramics, for binding carbon black, for binding fertilizers and herbicides, as a dust suppressant, in the making of plywood and particle board, for binding animal feeds, as a binder for fiberglass, as a binder in linoleum paste and as a soil stabilizer.

As a dispersant, the lignin or lignosulfonates can be used, e.g., concrete mixes, clay and ceramics, dyes and pigments, leather tanning and in gypsum board.

As an emulsifier, the lignin or lignosulfonates can be used, e.g., in asphalt, pigments and dyes, pesticides and wax emulsions.

As a sequestrant, the lignin or lignosulfonates can be used, e.g., in mico-nutrient systems, cleaning compounds and water treatment systems, e.g., for boiler and cooling systems.

As a heating source, lignin generally has a higher energy content than holocellulose (cellulose and hemicellulose) since it contains more carbon than homocellulose. For example, dry lignin can have an energy content of between about 11,000 and 12,500 BTU per pound, compared to 7,000 an 8,000 BTU per pound of holocellulose. As such, lignin can be densified and converted into briquettes and pellets for burning. For example, the lignin can be converted into pellets by any method described herein. For a slower burning pellet or briquette, the lignin can be crosslinked, such as applying a radiation dose of between about 0.5 Mrad and 5 Mrad. Crosslinking can make a slower burning form factor. The form factor, such as a pellet or briquette, can be converted to a "synthetic coal" or charcoal by pyrolyzing in the absence of air, e.g., at between 400 and 950° C. Prior to pyrolyzing, it can be desirable to crosslink the lignin to maintain structural integrity.

Accordingly, other embodiments are within the scope of the following claims.

What is claimed is:

1. A processing facility configured to process a lignocellulosic material comprising:
   an ionizing radiation system to treat the lignocellulosic material prior to fermentation, oxidizing equipment comprising a gas supply configured to provide an oxidizing environment of air or oxygen to the ionizing radiation system,
   a lignin content measurement system configured to measure a lignin content of the lignocellulosic material prior to fermentation,
   and a fermentation system to ferment a treated lignocellulosic material from the ionizing radiation system,
   wherein the ionizing radiation system comprises a dose or dose rate as an adjustable process parameter that can be adjusted, based on the lignin content determined by the lignin content measurement system, to reduce a recalcitrance of the lignocellulosic material.

2. The processing facility of claim 1, further including a mechanical treatment system to treat the lignocellulosic material prior to fermentation, wherein the mechanical treatment system includes a second adjustable process parameter that can be adjusted, based on the lignin content determined by the lignin content measurement system, to reduce the recalcitrance of the lignocellulosic material.

3. The processing facility of claim 1, wherein the ionizing radiation system comprises an electron beam irradiation device, the device configured to provide an electron beam having an energy of at least 1 MeV.

4. The processing facility of claim 1, further comprising a system configured for capturing lignin.

5. The processing facility of claim 1, wherein the facility is configured to process more than one type of lignocellulosic material.

6. The processing facility of claim 1, wherein the fermentation system comprises a fermentative microorganism.

7. The processing facility of claim 6, further comprising a saccharification system to saccharify the treated lignocellulosic material prior to fermentation.

8. The processing facility of claim 7, wherein the saccharification system comprises a cellulase.

* * * * *